(12) United States Patent
Needham et al.

(10) Patent No.: US 12,014,490 B2
(45) Date of Patent: Jun. 18, 2024

(54) SYSTEMS AND METHODS OF VALIDATION OF RAPID TEST DEVICE RESULTS

(71) Applicant: INBIOS INTERNATIONAL, INC., Seattle, WA (US)

(72) Inventors: James William Needham, Seattle, WA (US); Koji Abe, Seattle, WA (US)

(73) Assignee: INBIOS INTERNATIONAL, INC., Seattle, WA (US)

( * ) Notice: Subject to any disclaimer, the term of this patent is extended or adjusted under 35 U.S.C. 154(b) by 331 days.

(21) Appl. No.: 17/235,757

(22) Filed: Apr. 20, 2021

(65) Prior Publication Data

US 2021/0327056 A1 Oct. 21, 2021

Related U.S. Application Data

(60) Provisional application No. 63/013,346, filed on Apr. 21, 2020.

(51) Int. Cl.
*G06K 9/00* (2022.01)
*G01N 33/48* (2006.01)
(Continued)

(52) U.S. Cl.
CPC ........... *G06T 7/0012* (2013.01); *G01N 33/48* (2013.01); *G06T 5/50* (2013.01); *G16H 10/40* (2018.01);
(Continued)

(58) Field of Classification Search
CPC ............ G06T 7/0012; G06T 5/50; G06T 2207/10024; G06T 2207/20081; G06T 2207/10016; G06T 2207/30072; G06T 7/30; G06T 7/90; G01N 33/48; G01N 33/54387; G16H 10/40; G16H 30/40; G16H 50/20; G16H 10/60; G16H 40/67; G16H 50/30; G16H 40/63; G16H 50/70; G16H 15/00; G16H 40/20; G16H 20/10; G16H 80/00; G16H 30/20; G16H 50/50; G16H 20/40; G16H 70/20; G06N 20/00; G06N 3/08; G06N 3/045; G06N 5/01;
(Continued)

(56) References Cited

U.S. PATENT DOCUMENTS 10,267,743 B2 * 4/2019 Burg .................. G01N 21/79
2012/0063652 A1 * 3/2012 Chen .................. G06V 10/56
382/128

(Continued)

*Primary Examiner* — Alex Kok S Liew
(74) *Attorney, Agent, or Firm* — Seed IP Law Group LLP

(57) ABSTRACT

Embodiments are directed to use of a rapid-test-validation computing device to determine if a result of a rapid test device is valid and identify the result. The rapid-test-validation computing device captures images of the rapid test device and employs a first artificial intelligence mechanism to determine if the rapid test device is properly aligned in the images. The rapid-test-validation computing device then employs a second artificial intelligence mechanism to determine if a result of the rapid test device is valid or invalid. If the result is valid, the rapid-test-validation computing device employs a third artificial intelligence mechanism to determine and present an objective output of the rapid test device result to a user; otherwise, the rapid-test-validation computing device presents a notification to the user that the rapid test device result is invalid.

19 Claims, 9 Drawing Sheets

(51) Int. Cl.
 *G06T 5/50* (2006.01)
 *G06T 7/00* (2017.01)
 *G16H 10/40* (2018.01)

(52) U.S. Cl.
 CPC ............ *G06T 2207/10024* (2013.01); *G06T 2207/20081* (2013.01)

(58) Field of Classification Search
 CPC .......... G06N 7/01; G06N 20/20; G06N 3/044; G06N 3/084; G06N 20/10; G06N 5/02; G06N 3/02; G06N 3/006; G06N 5/041; G06N 3/0464; G06N 3/088; G06V 20/44; G06V 20/40; G06V 20/41; G06V 20/20; G06V 20/52; G06V 40/10
 See application file for complete search history.

(56) References Cited

U.S. PATENT DOCUMENTS

| | | | | |
|---|---|---|---|---|
| 2013/0303869 | A1* | 11/2013 | Rebec | A61B 5/1459 600/365 |
| 2015/0359458 | A1* | 12/2015 | Erickson | A61B 5/14539 382/133 |
| 2016/0148079 | A1* | 5/2016 | Shen | G06V 10/454 382/157 |
| 2018/0107789 | A1* | 4/2018 | Pulitzer | G16H 50/30 |
| 2019/0027251 | A1* | 1/2019 | Pulitzer | G16H 30/40 |

\* cited by examiner

SYSTEMS AND METHODS OF VALIDATION OF RAPID TEST DEVICE RESULTS

TECHNICAL FIELD

The present disclosure relates generally to testing validation, and more particularly to utilizing artificial intelligence mechanisms to validate and identify rapid test device results.

BACKGROUND

Description of the Related Art

Medical practitioners often use rapid test devices to determine the presence or absence of a biologically relevant target in a blood or fluid sample. These rapid test devices often output the results via a line, series of dots, or particular color-coded response. For example, a line at a first location on the rapid test device may indicate the presence of the biologically relevant target in the sample, whereas as a line at a second location on the rapid test device may indicate the absence of the biologically relevant target in the sample. Unfortunately, these rapid test devices often output partial or inconclusive results. For example, instead of a line, the rapid test device may output a dot or a series of dots at the location where the line should appear. This output may be an indication of an inconclusive result, too small of a sample, or a malfunctioning rapid test device. The medical practitioner, however, may view the dots as a valid result, which would be an incorrect reading of the results and could cause an inaccurate diagnosis. Moreover, the outputs of some rapid test devices may be color coded with each color representing a different result. Some medical practitioners, however, may not correctly identify the color being displayed depending on how prominent the color is being displayed, the lighting under which the medical practitioner is viewing the rapid test device, vision difficulties of the medical practitioner, or other factors. It is with respect to these and other considerations that the embodiments described herein have been made.

BRIEF DESCRIPTION OF THE SEVERAL VIEWS OF THE DRAWINGS

Non-limiting and non-exhaustive embodiments are described with reference to the following drawings. In the drawings, like reference numerals refer to like parts throughout the various figures unless otherwise specified.

For a better understanding of the present disclosure, reference will be made to the following Detailed Description, which is to be read in association with the accompanying drawings.

DETAILED DESCRIPTION

The following description, along with the accompanying drawings, sets forth certain specific details in order to provide a thorough understanding of various disclosed embodiments. However, one skilled in the relevant art will recognize that the disclosed embodiments may be practiced in various combinations, without one or more of these specific details, or with other methods, components, devices, materials, etc. In other instances, well-known structures or components that are associated with the environment of the present disclosure, including but not limited to the communication systems and networks, have not been shown or described in order to avoid unnecessarily obscuring descriptions of the embodiments. Additionally, the various embodiments may be methods, systems, media, or devices. Accordingly, the various embodiments may be entirely hardware embodiments, entirely software embodiments, or embodiments combining software and hardware aspects.

Throughout the specification, claims, and drawings, the following terms take the meaning explicitly associated herein, unless the context clearly dictates otherwise. The term "herein" refers to the specification, claims, and drawings associated with the current application. The phrases "in one embodiment," "in another embodiment," "in various embodiments," "in some embodiments," "in other embodiments," and other variations thereof refer to one or more features, structures, functions, limitations, or characteristics of the present disclosure, and are not limited to the same or different embodiments unless the context clearly dictates otherwise. As used herein, the term "or" is an inclusive "or" operator, and is equivalent to the phrases "A or B, or both" or "A or B or C, or any combination thereof," and lists with additional elements are similarly treated. The term "based on" is not exclusive and allows for being based on additional features, functions, aspects, or limitations not described, unless the context clearly dictates otherwise. In addition, throughout the specification, the meaning of "a," "an," and "the" include singular and plural references.

Figure 1:
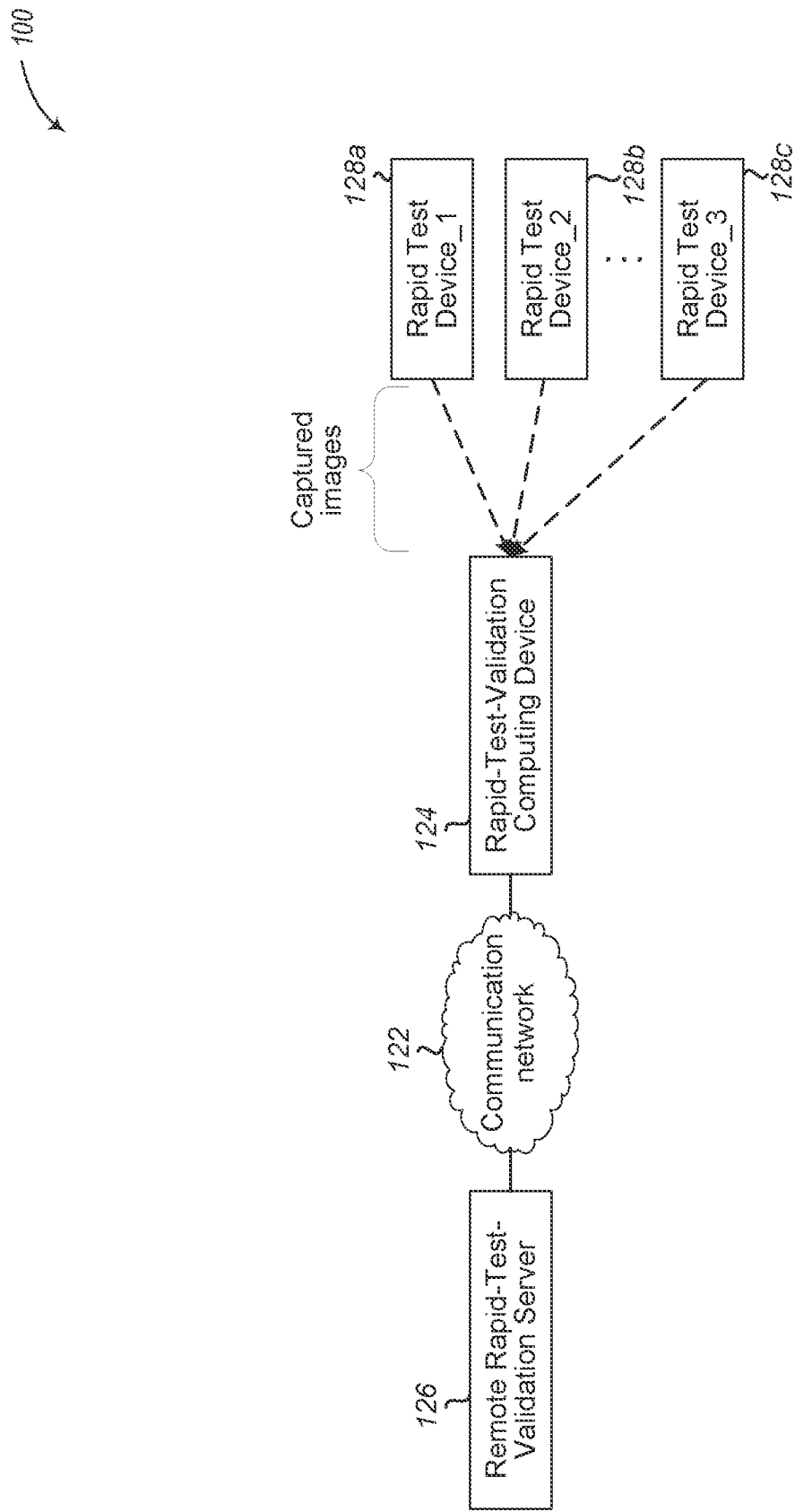
FIG. 1 illustrates a context diagram of an environment for validating rapid test device results in accordance with embodiments described herein.

FIG. 1 illustrates a context diagram of an environment 100 for validating rapid test device results in accordance with embodiments described herein. Environment 100 includes a rapid-test-validation computing device 124 and one or more rapid test devices 128a-128c (individually and collectively referred to as rapid test device 128).

The rapid test devices 128a-128c are testing devices that present visual cues as to a particular result. In general, the rapid test devices 128a-128c present an output in response to the presence or absence of a biologically relevant target. Examples of the rapid test devices 128a-128c may include, but are not limited to, a lateral flow immunoassay, flow through assay, ELISA plate or other similar test device comprising a colorimetric, fluorometric, or other optically sensitive reagent that is indicative of the presence or absence of a biologically relevant target (e.g., a protein, nucleic acid sequence, antibody, virus, etc.).

The rapid test devices 128a-128c include one or multiple test lines, one or multiple side-by-side dipsticks, or one or multiple side-by-side cassettes, or the like. The rapid test devices 128a-128c may include arrays of spots, lines or other relevant shapes necessary for the test devices. Although embodiments described herein describe the rapid test devices 128a-128c as indicating whether a biologically relevant target is present or absent, embodiments are not so limited and the rapid test devices 128a-128c may also be used to indicate other reactive targets, such as pH levels (e.g., in soil), chlorine levels (e.g., in pools), etc.

The rapid-test-validation computing device 124 captures one or more images of the rapid test device 128 via a camera (not illustrated). The rapid-test-validation computing device 124 utilizes a first artificial intelligence mechanism to determine if a position of the rapid test device 128 in the captured images is acceptable for processing, such as if it is in a particular position or within a threshold variance of a reference position. In some embodiments, the rapid-test-validation computing device 124 may also augment the captured images by overlaying a semi-transparent reference or representation of the rapid test device 128 to enable the user to properly align the rapid-test-validation computing device 124 with the rapid test device 128. In some embodiments, a plurality of images are captured and displayed to the user in real time to allow the user to move the position of the rapid test device 128 or the rapid-test-validation computing device 124 for proper alignment.

Although embodiments are described herein as using an artificial intelligence mechanism to determine a position of the rapid test device (or a color validation sheet), embodiments are not so limited. Rather, other techniques for tracking objects in images may be used, such as edge or shadow detection.

In some embodiments, the rapid-test-validation computing device 124 may utilize the previously captured image that included the properly aligned rapid test device 128 for further processing. In other embodiments, the rapid-test-validation computing device 124 may capture another image in response to manual user input or automatically, such as when the rapid test device 128 is properly aligned.

If the rapid test device 128 is positioned properly in at least one of the captured images, the rapid-test-validation computing device 124 utilizes a second artificial intelligence mechanism on the image to determine if a result of the rapid test device 128 is valid or invalid. If the result is valid, the rapid-test-validation computing device 124 may utilize a third artificial intelligence mechanism on the image to determine an objective characterization of the results (e.g., "positive," "negative," etc.). The rapid-test-validation computing device 124 displays the objective characterization of the results to a user of the rapid-test-validation computing device 124. The rapid-test-validation computing device 124 also displays information indicating if the result of the rapid test device 128 is valid or invalid.

In some embodiments, the rapid-test-validation computing device 124 determines and displays the objective characterization of the results and the valid/invalid determination in real time as the user is using the rapid-test-validation computing device 124 to capture images of the rapid test device 128. In other embodiments, the rapid-test-validation computing device 124 may capture images of one or more rapid test devices 128 for post-processing and display to a user. In various embodiments, the rapid-test-validation computing device 124 may transmit or upload the validation and objective results, along with the captured images, to one or more other computing devices for storage or review. These results can be used to further train or refine the artificial intelligence mechanisms used herein. Examples of such other computing devices may include remote rapid-test-validation server 126, cloud computing resources, or other remote computing devices that maintain patient data. In some embodiments, an identifier or lot number of the rapid test device may be stored with the results, which can be used to determine if a particular rapid test device lot or batch is defective, e.g., due to erroneous results.

In some embodiments, a user may use the rapid-test-validation computing device 124 to select a rapid test device for processing. The user may select the appropriate rapid test device from a list of possible rapid test devices or the user may scan a machine readable symbol (e.g., barcode, QR code, etc.) or other identifier of the rapid test device. In at least one embodiment, the rapid-test-validation computing device 124 may be configured to start or utilize a timer for the selected rapid test device. For example, if the rapid test device requires 20 minutes to complete a test and output a result, then the rapid-test-validation computing device 124 may utilize a timer so as to not process the rapid test device until after the timer has expired. In this way, the rapid-test-validation computing device 124 does not process a rapid test device and output a result before the rapid test device has completed its test. Likewise, the same timer or a second timer may establish a window of time in which to process the rapid test device. This time window may be used to ensure the rapid test device is not process too late.

Examples of the rapid-test-validation computing device 124 include, but are not limited to, smartphones, tablet computers, desktop or laptop computers in communication with a camera, wearable computers, or other computing devices that have or are in communication with a camera.

In some embodiments, the environment 100 may optionally include a remote rapid-test-validation server 126. In various embodiments, the remote rapid-test-validation server 126 may perform many of the embodiments described herein as being performed by the rapid-test-validation computing device 124. In at least one embodiment, the rapid-test-validation computing device 124 may capture images of the rapid test devices 128 and transmit the captured images to the remote rapid-test-validation server 126 via communication network 122 for processing. The communication network 122 includes one or more wired or wireless, or a combination of wired and wireless, data communication networks. The remote rapid-test-validation server 126 may output the results to a user via a display device (not illustrated) or may transmit the results back to the rapid-test-validation computing device 124 for display.

Figure 2:
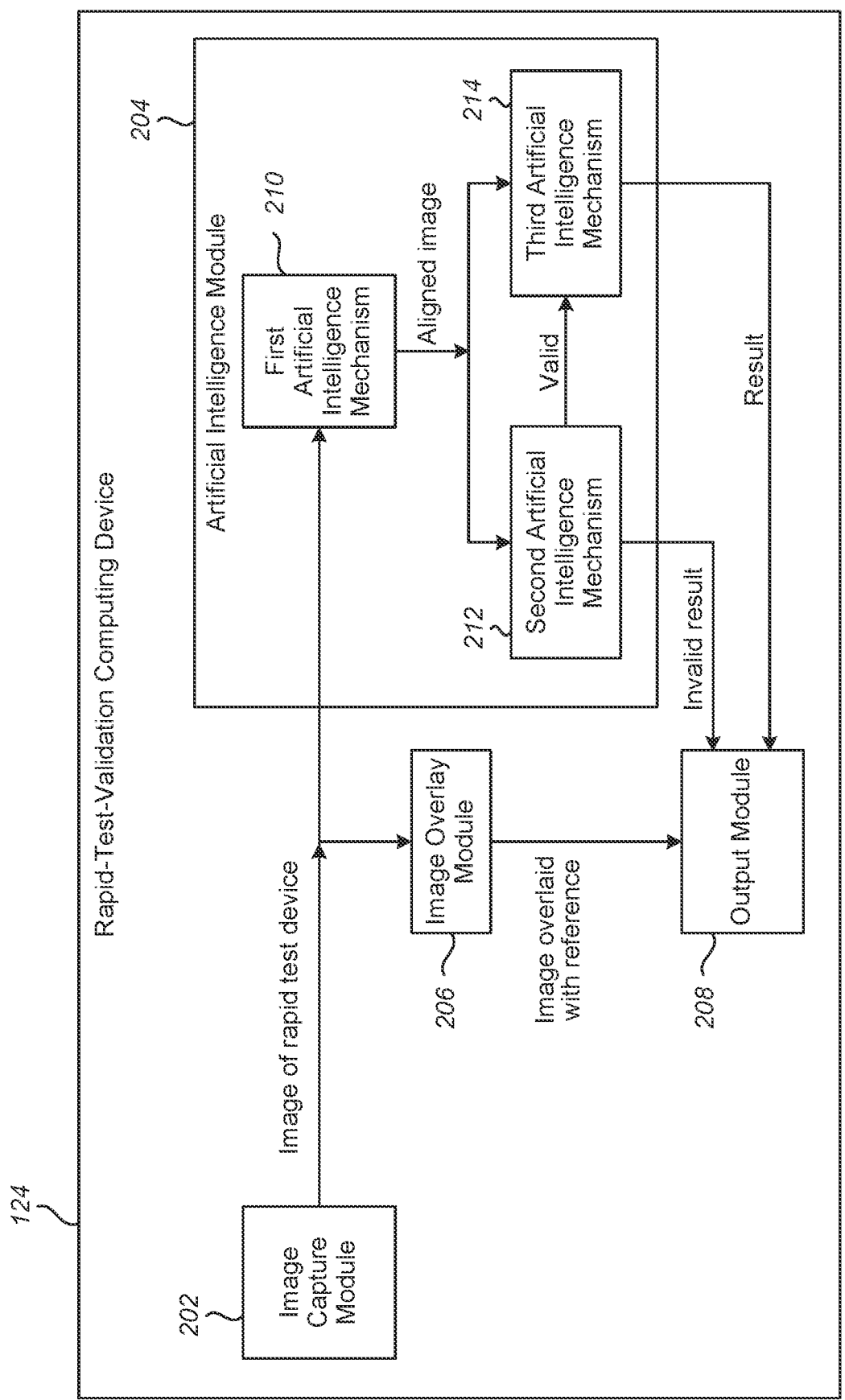
FIG. 2 illustrates a system diagram of a rapid-test-validation computing device in accordance with embodiments described herein.

FIG. 2 illustrates a system diagram of a rapid-test-validation computing device 124 in accordance with embodiments described herein. The system components of the rapid-test-validation computing device 124 illustrated in FIG. 2 are for illustrative purposes and are not to be limiting. Moreover, the functionality of one or more of the illustrated system components may be combined into fewer components or separated in more components than what is shown.

In this illustrated example, the rapid-test-validation computing device 124 includes an image capture module 202, an artificial intelligence module 204, an image overlay module 206, and an output module 208. The image capture module 202 performs embodiments described herein to capture or obtain images of one or more rapid test devices. The captured images are provided from the image capture module 202 to the artificial intelligence module 204 and to the image overlay module 206. The image overlay module 206 modifies or augments the captured images to overlay a semi-transparent reference or representation of the rapid test device. The modified images are provided from the image overlay module 206 to the output module 208 for presentation to a user.

The artificial intelligence module 204 includes a first artificial intelligence mechanism 210, a second artificial intelligence mechanism 212, and a third artificial intelligence mechanism 214. The first artificial intelligence mechanism 210 determines if the rapid test device is properly aligned in the captured image. The second artificial intelligence mechanism 212 determines if one or more results on the rapid test device are valid or invalid. If the results are invalid, the artificial intelligence module 204 presents the invalid determination to a user via the output module 208. The third artificial intelligence mechanism 214 determines an objective characterization of the valid results. The artificial intelligence module 204 presents the object characterization of the results to the user via the output module 208. In some embodiments, the artificial intelligence module 204 may instruct the image capture module 202 to capture additional images of the rapid test device, such as if the rapid test device is not properly positioned in the captured images.

In some embodiments, the output module 208 displays information to a user of the rapid-test-validation computing device 124 via a display device. In other embodiments, the output module 208 transmits the results information to another computing device, such as remote rapid-test-validation server 126, for display, storage, or further processing (e.g., comparing a plurality of results from a plurality rapid test device).

The operation of certain aspects will now be described with respect to FIGS. 3 and 4. In at least one of various embodiments, processes 300 and 400 described in conjunction with FIGS. 3 and 4, respectively, may be implemented by one or more processors or executed via circuitry on one or more computing devices, such as rapid-test-validation computing device 124 of FIG. 1 or remote rapid-test-validation server 126 of FIG. 1.

Figure 3:
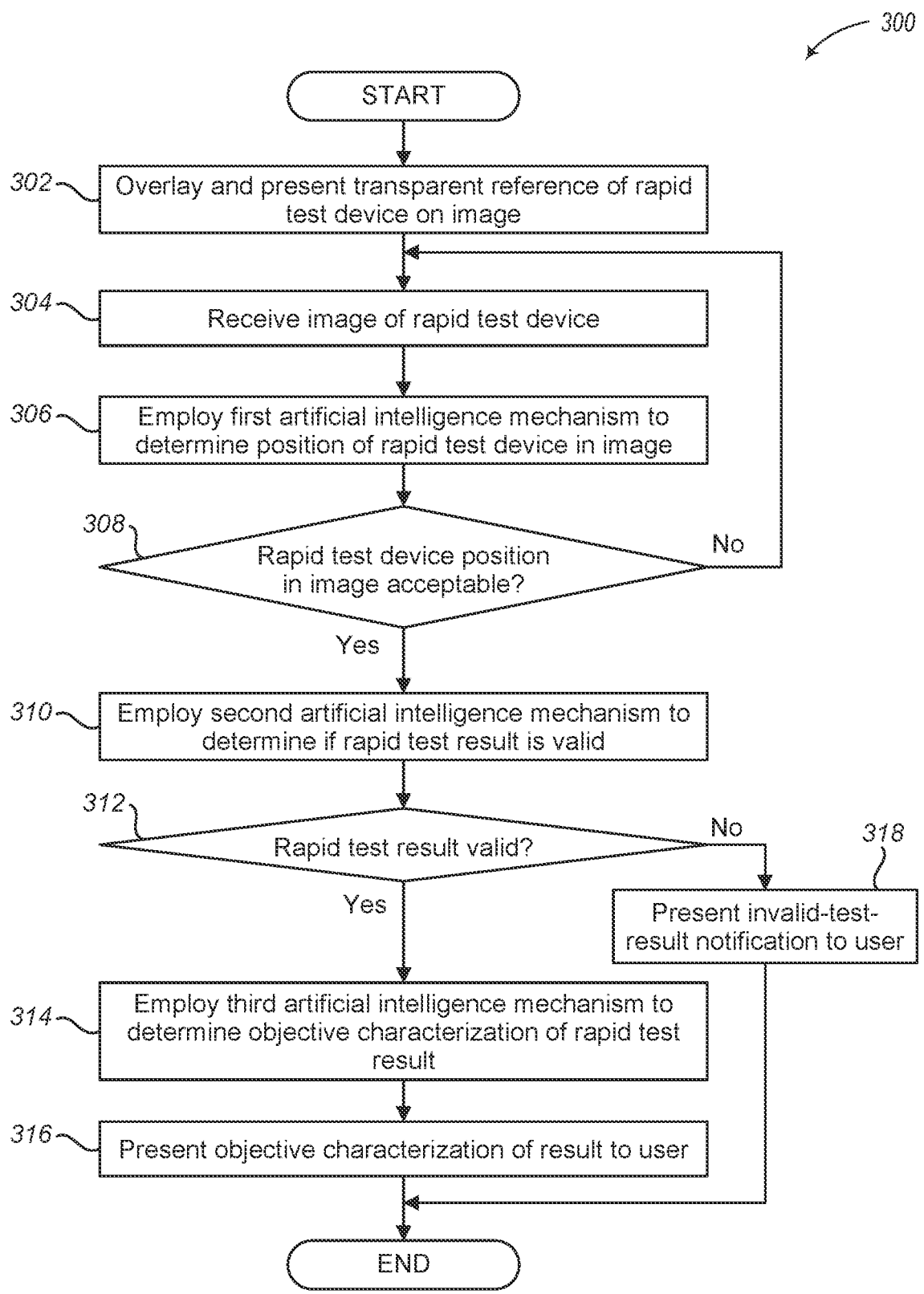
FIG. 3 illustrates a logical flow diagram showing one embodiment of a process for capturing images of a rapid test device and employing artificial intelligence mechanisms to validate results in accordance with embodiments described herein.

FIG. 3 illustrates a logical flow diagram showing one embodiment of a process 300 for capturing images of a rapid test device 128 and employing artificial intelligence mechanisms to validate results in accordance with embodiments described herein.

Process 300 begins, after a start block, at block 302, where a transparent reference of a rapid test device is presented to a user as being overlaid on images captured by the rapid-test-validation computing device. In some embodiments, the overlaid image is displayed to the user via a graphical user interface. In other embodiments, the overlaid image is transmitted or sent to another computing device for display to the user.

The transparent reference is a partially transparent representation of the rapid test device being validated and may be referred to as the rapid-test-device reference. The transparent reference provides a visual cue to a user as to an ideal position for the rapid test device to be within the images for proper processing and analysis.

In some embodiments, the particular type of rapid-test-device reference is selected by a user. In at least one embodiment, a list of possible rapid-test-device references is presented to the user. The user can then select the rapid-test-device reference that matches or corresponds to the rapid test device being validated. In other embodiments, an artificial intelligence mechanism is employed on the received image to select the rapid-test-device reference. In yet other embodiments, the artificial intelligence mechanism may be employed to determine a set of possible rapid-test-device references, which is then presented to the user. The user is then prompted to select the particular rapid-test-device reference of the rapid test device being validated. In some other embodiments, a machine readable symbol (e.g., barcode or QR code) or other identifying information on the rapid test device, or the packaging of the rapid test device, may be scanned to identify or select the rapid-test-device reference.

In embodiments where the image includes a plurality of rapid test devices, a plurality of rapid-test-device references may be overlaid on the received image. In some embodiments, the positioning of the plurality of rapid-test-device references in the overlaid image may be determined based on the positioning of the rapid test devices being validated within the received image, such as by employing a plurality of machine learning models trained to identify different rapid test devices and their locations within an image.

Process 300 proceeds to block 304, where an image of a rapid test device is received. In some embodiments, the image is captured by the device executing process 300, e.g., rapid-test-validation computing device 124. In other embodiments, the image is captured by a device remote from the device executing process 300, e.g., rapid-test-validation server 126. In some embodiments, the image may include a plurality of rapid test devices.

Process 300 continues at block 306, where a first artificial intelligence mechanism is employed to determine a position of the rapid test device in the received image. In some embodiments, the first artificial intelligence mechanism is a machine learning model trained to identify the rapid test device in an image. In other embodiments, the first artificial intelligence mechanism stores one or more characteristics of rapid test devices in which to compare with the received image.

Process 300 proceeds next to decision block 308, where a determination is made whether the position of the rapid test device in the received image is acceptable. In some embodiments, the positioning of the rapid test device in the image is acceptable when the first artificial intelligence mechanism identifies the rapid test device in the image. In other embodiments, the position of the rapid test device in the image is acceptable when the first artificial intelligence mechanism indicates that the rapid test device is positioned within a selected threshold size, rotation, and tilt of the rapid-test-device reference. If the position of the rapid test device in the image is acceptable, process 300 flows to block 310; otherwise, process 300 loops to block 302 to continue to receive additional images of the rapid test device.

In some embodiments when process 300 loops to block 302, an instruction may be presented to the user indicating advice on how to better position the rapid test device within the image. The looping of process 300 may enable a plurality of images to be captured as a video to be displayed to the user in real time so that the user can move the physical rapid test device (or camera) in a way to align the physical rapid test device with the rapid-test-device reference overlaid on the video. Once aligned, one or more images can be captured to be further analyzed by process 300. These images can be captured in response to manual input from the user, or they may be automatically captured when the system determines that the position of the rapid test device relative to the camera is acceptable.

At block 310, a second artificial intelligence mechanism is employed to determine if the rapid test result is valid. In some embodiments, the second artificial intelligence mechanism is a machine learning model trained to classify valid or invalid test results output by the rapid test device. In other embodiments, the second artificial intelligence mechanism stores one or more characteristics of valid and invalid rapid-test-device results in which to compare with the received image.

Figures 5A, 5B:
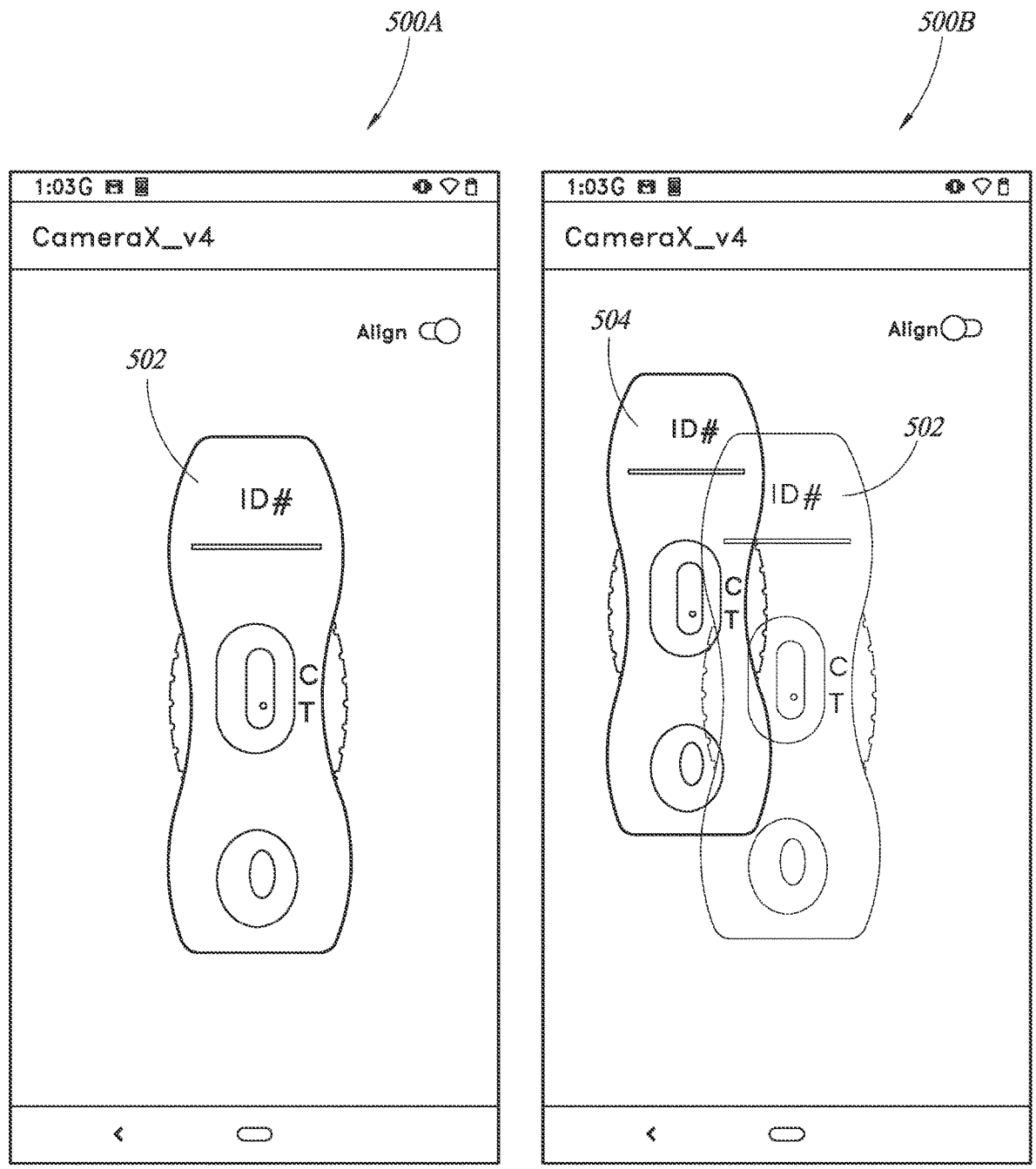
FIGS. 5A-5D illustrate use case examples of graphical user interfaces presenting information to a user with respect to validating rapid test device results in accordance with embodiments described herein.
Figures 5C, 5D:
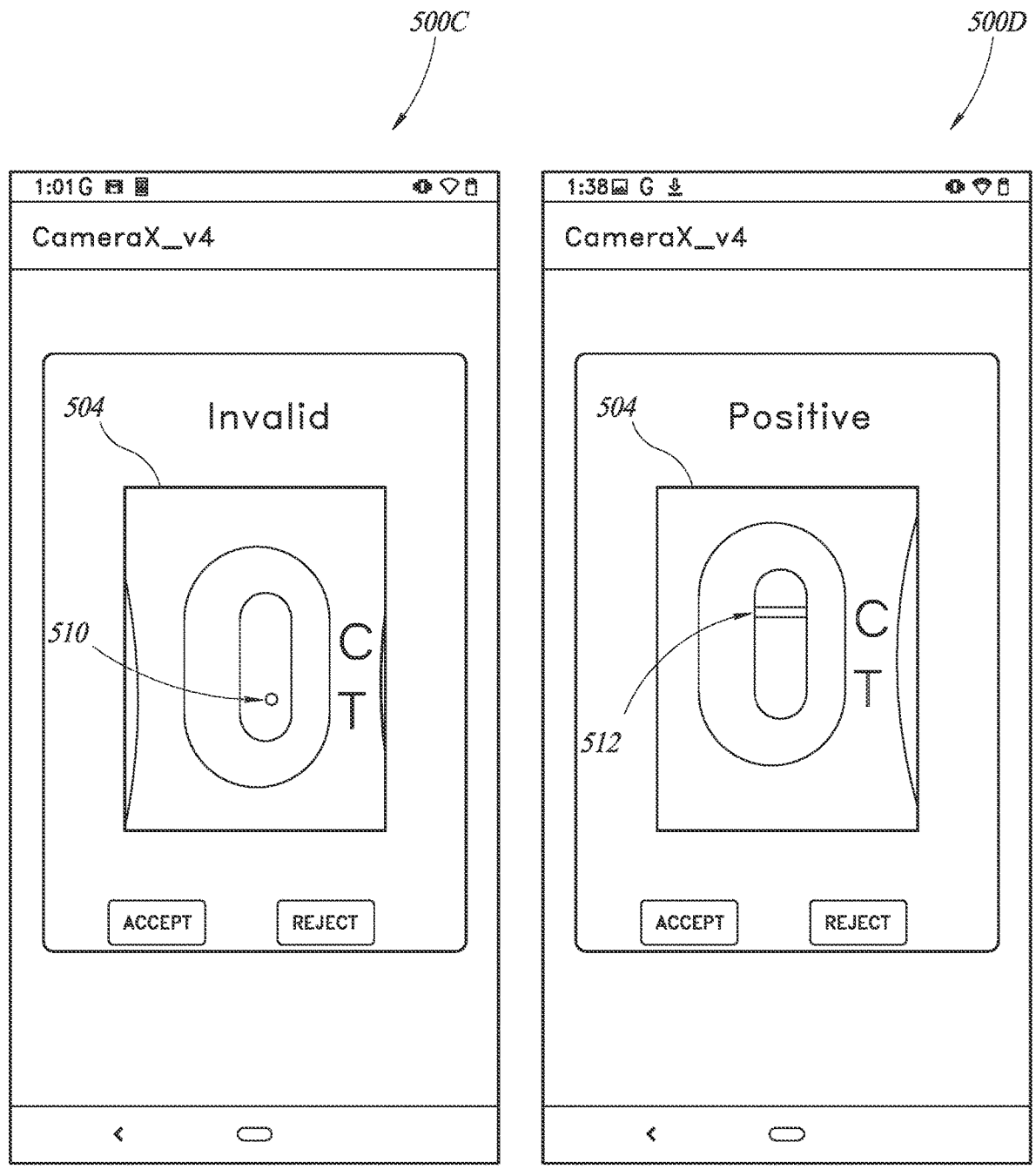

For example, a valid test result may be a full-length control line across a test output area of the rapid test device, e.g., as shown in FIG. 5D. In comparison, an invalid test result may be a dot within some portion of the test output area of the rapid test device, e.g., as shown in FIG. 5C. In other embodiments, valid or invalid test results may be identifiable by color, intensity, alphanumeric codes, etc.

In various embodiments, a plurality of second artificial intelligence mechanisms are generated for corresponding rapid test devices of a plurality of different rapid test devices. A particular second artificial intelligence mechanism is selected from the plurality of artificial intelligence mechanisms based on the rapid test device selected or identified at block 304. This selected second artificial intelligence mechanism is then utilized with respect to the corresponding rapid test device in the received image.

In some embodiments, a single rapid test device may have multiple output areas with different results. In at least one such embodiment, different second artificial intelligence mechanisms are generated for each corresponding output area of the rapid test device and employed on the received image to determine if results in each separate output area are valid or invalid.

Process 300 continues next at decision block 312, where a determination is made whether the rapid test results are valid based on the employment of the second artificial intelligence mechanism. If the test results are valid, process 300 flows to block 314; otherwise, process 300 flows to block 318 to present an invalid-test-result notification to the user via a graphical user interface. In some embodiments, the invalid-test-result notification may indicate the result "invalid," similar to what is shown in FIG. 5C. In other embodiments, the invalid-test-result notification may provide additional information indicating whether the sample was too small or tainted, or if the rapid test device malfunctioned.

At block 314, a third artificial intelligence mechanism is employed to determine an objective characterization of the rapid test device result. In some embodiments, the third artificial intelligence mechanism is a machine learning model trained to classify possible test results output by the rapid test device. In other embodiments, the third artificial intelligence mechanism stores one or more characteristics of each possible test result of the rapid test device in which to compare with the received image.

For example, a positive test result may be a full-length control line across a first portion of a test output area of the rapid test device, whereas a negative test result may be a full-length control line across a second portion of the test output area of the rapid test device. In other embodiments, different objective results may be identifiable by color, intensity, alphanumeric codes, etc.

In various embodiments, a plurality of third artificial intelligence mechanisms are generated for corresponding rapid test devices of a plurality of different rapid test devices. A particular third artificial intelligence mechanism is selected from the plurality of artificial intelligence mechanisms based on the rapid test device selected or identified at block 304. This selected third artificial intelligence mechanism is then utilized with respect to the corresponding rapid test device in the received image to identify the corresponding results.

As mentioned above, a single rapid test device may have multiple output areas with different results. In at least one embodiment, different third artificial intelligence mechanisms are generated for each corresponding output area of the rapid test device and employed on the received image to determine the objective characterization of the results in each separate output area.

Process 300 proceeds next to block 316, where the objective characterization of the test results are presented to a user. In some embodiments, the results are displayed to the user via a graphical user interface. In other embodiments, the results are transmitted or sent to another computing device for display to the user. The displayed objective characterization may be qualitative or binary result, such as "positive" or "negative," or it may be semi-quantitative, such as a maximum value, mean signal strength, numeric value (e.g., '0', '1', '2'), etc. In some embodiments, a confidence level or value of the objective characterization may be determined and displayed to the user.

After block 316 or after block 318, process 300 terminates or otherwise returns to a calling process to perform other actions. In some embodiments, process 300 may loop (not illustrated) to block 302 to receive new images of another rapid test device.

In some embodiments, the image of the rapid test device may be pre-processed before employing one or more of the artificial intelligence mechanisms. For example, in some embodiments, a portion of each type of rapid test device may have a known average color channel signal. The image can then be processed using an auto-white processing to scale or adjust the image to the known average color channel signal. This pre-processing can improve the accuracy of the artificial intelligence mechanisms because the artificial intelligence mechanisms are employed on images having similarly colored rapid test devices. In some other embodiments, this pre-processing may also be utilized to determine if the color validation process described in FIG. 4 is to be utilized. If the average color channel signal exceeds a select threshold from the known average color channel signal for the rapid test device, then the system may determine that the color validation process is to be performed before further processing of the rapid test device.

Figure 4:
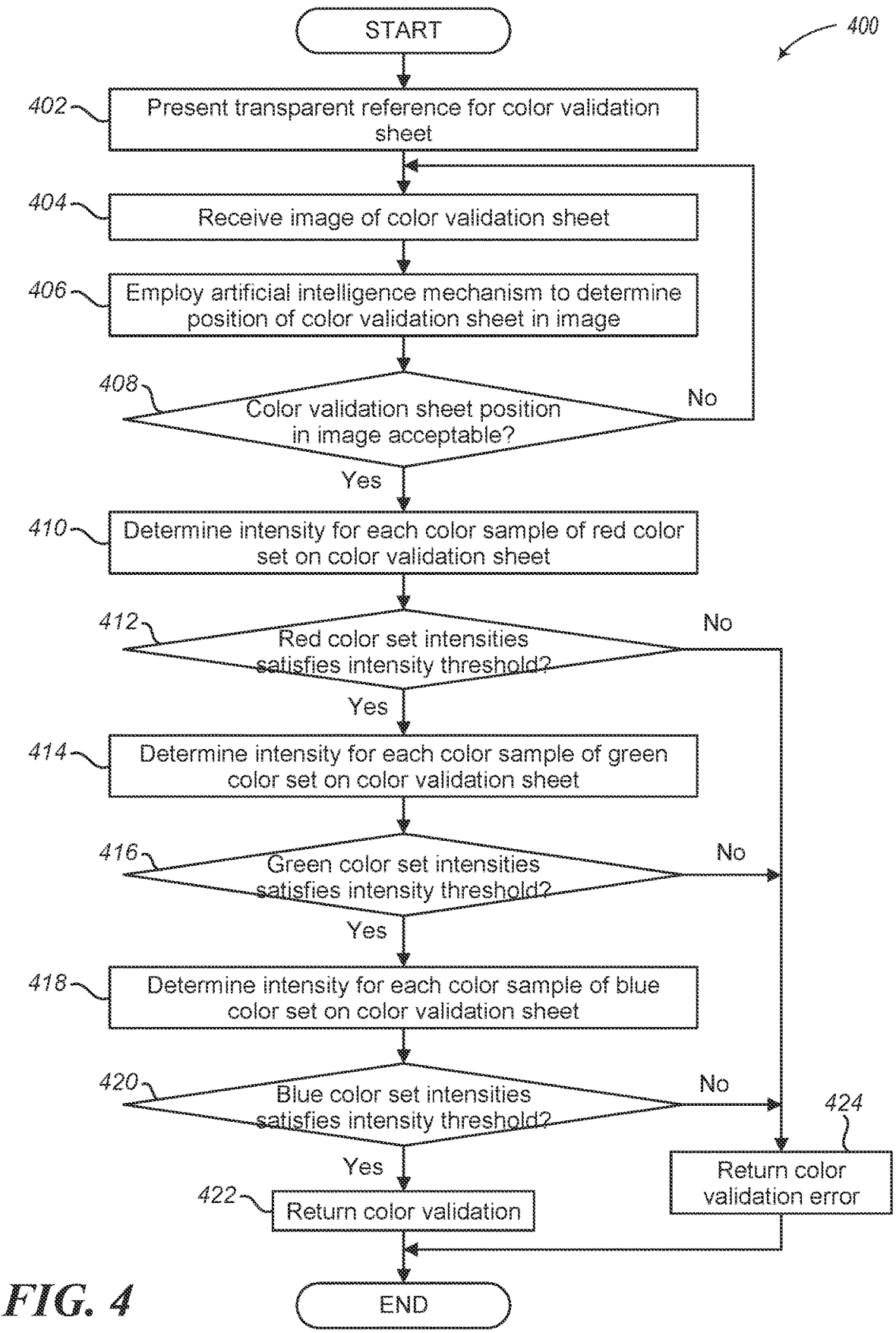
FIG. 4 illustrates a logical flow diagram showing one embodiment of a process for capturing images of a color validation sheet and employing artificial intelligence mechanisms to validate camera colors in accordance with embodiments described herein.

FIG. 4 illustrates a logical flow diagram showing one embodiment of a process 400 for capturing images of a color validation sheet and employing artificial intelligence mechanisms to validate camera colors in accordance with embodiments described herein.

In some embodiments, a user may select or input a request to perform the color validation process. In other embodiments, the color validation process may be automatically requested at select or predetermined times, such as prior to the first analysis of a rapid test device, after a threshold number of rapid test devices have been analyzed, when a user selects a new type of rapid test device, after a select amount of time has lapsed, etc. In yet other embodiments, the color validation process may be automatically performed in response to detection of a threshold image condition during the analysis of a rapid test device. For example, if a rapid test device is a known color, but a different color is detected in an initial image or in a plurality of images, such as images captured at block 302 in FIG. 3, then the color validation process may commence. In these situations, the lighting—such as low-light conditions, utilization of red lighting or other non-white lighting, etc.—may impact the accuracy of one or more of the artificial intelligence mechanism employed in process 300 in FIG. 3. Accordingly, the color validation process may be employed to determine if the lighting has the potential to impact the analysis of a rapid test device.

Process 400 begins, after a start block, at block 402, where a transparent reference of a color validation sheet is presented to a user as being overlaid on images captured by the rapid-test-validation computing device. In some embodiments, the overlaid image is displayed to the user via a graphical user interface. In other embodiments, the overlaid images are transmitted or sent to another computing device for display to the user.

In some embodiments, the transparent reference is an alignment frame, but contains no other visual representations of a color validation sheet. In other embodiments, the transparent reference is a partially transparent representation of the color validation sheet. The transparent reference provides a visual cue to a user as to an ideal position for the color validation sheet to be within the image for proper processing and analysis.

Process 400 proceeds to block 404, where an image of a color validation sheet is received. In some embodiments, the image is captured by the device executing process 300 in FIG. 3, e.g., rapid-test-validation computing device 124. The color validation sheet includes a plurality of different color samples having different intensities. In at least one embodiment, the color validation sheet includes seven color samples of different intensities for a plurality of different colors, such as red, green, and blue. Accordingly, the color validation sheet includes seven red color samples, seven green color samples, and seven blue colors samples, where each sample of each color has a different intensity. Other colors and numbers of color samples may also be utilized.

Figure 6A:
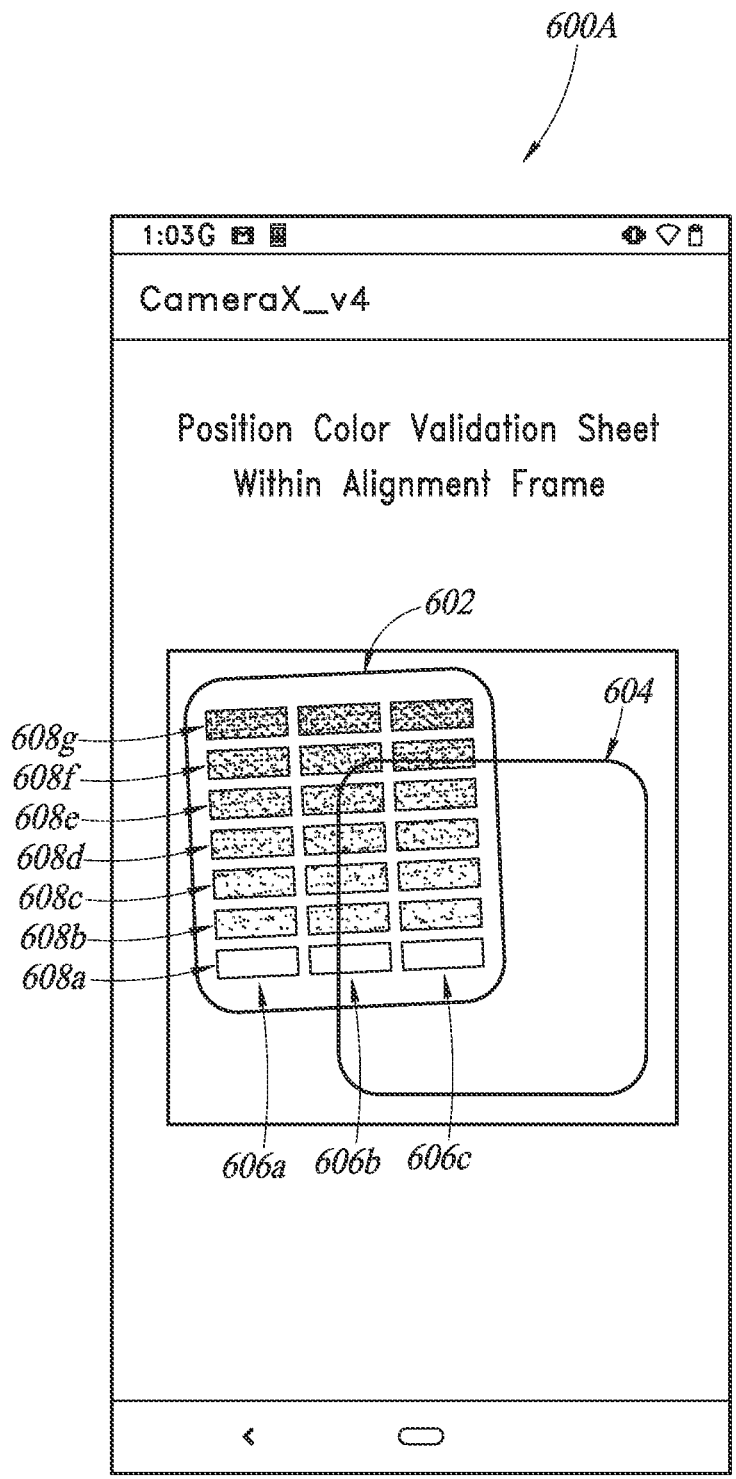
FIGS. 6A-6B illustrate use case examples of graphical user interfaces presenting information to a user with respect to validating camera colors prior to validating rapid test device results in accordance with embodiments described herein.

An example of a color validation sheet is shown in FIG. 6A. Although FIG. 6A is in grayscale, the left-most column may be red, the center column may be green, and the right column may be blue, where the top row includes the highest intensity colors, the bottom row includes the lowest intensity colors, and the rows between the top and bottom include degrading intensity colors from top to bottom. This example arrangement of colors and intensities is not limiting, and other embodiments could have different arrangements of colors and intensities. Additional details is discussed below in conjunction with FIG. 6A.

Process 400 continues at block 406, where an artificial intelligence mechanism is employed to determine a position of the color validation sheet in the received image. In some embodiments, the artificial intelligence mechanism is a machine learning model trained to identify the color validation sheet in an image. In other embodiments, the artificial intelligence mechanism stores one or more characteristics of the color validation sheet with which to compare with the received image. In yet other embodiments, an object tracking mechanism may be employed to detect a position of the color validation sheet in the image relative to the transparent reference or alignment frame.

Process 400 proceeds next to decision block 408, where a determination is made whether the position of the color validation sheet in the received image is acceptable. In some embodiments, the positioning of the color validation sheet in the image is acceptable when the artificial intelligence mechanism identifies the color validation sheet in the image. In other embodiments, the position of the color validation sheet in the image is acceptable when the artificial intelligence mechanism indicates that the color validation sheet is positioned within a selected threshold size, rotation, or tilt relative to the transparent reference. If the position of the color validation sheet in the image is acceptable, process 400 flows to block 410; otherwise, process 400 loops to block 402 to continue to receive additional images of the color validation sheet.

In some embodiments when process 400 loops to block 402, an instruction may be presented to the user indicating advice on how to better position the color validation sheet within the image. The looping of process 400 may enable a plurality of images to be captured as a video to be displayed to the user in real time so that the user can move the physical color validation sheet (or camera) in a way to align the physical color validation sheet with the transparent reference or alignment frame overlaid on the video. Once aligned, one or more images can be captured to be further analyzed by process 400. These images can be captured in response to manual input from the user, or they may be automatically captured when the system determines that the position of the color validation sheet relative to the camera is acceptable.

At block 410, an intensity of each of a plurality of color samples of a red color set on the color validation sheet is determined. As mentioned above, the color validation sheet includes a plurality of different color samples, each having a different intensity, for multiple colors. In at least one embodiment, the color validation sheet includes seven different red sample intensities. The intensity of each of these sample colors is calculated.

Process 400 proceeds next to decision block 412, where a determination is made whether the intensities for the red color set satisfy one or more intensity thresholds. In some embodiments, each sample color in the red color set corresponds to a separate intensity threshold. Each corresponding threshold may be a single intensity value, a range of intensity values, or an intensity value with a tolerance level. In this way, each separate calculated color sample intensity is compared to the corresponding threshold for that color sample. In some embodiments, the intensity threshold is satisfied if each separate color sample intensity threshold is satisfied. In other embodiments, the intensity threshold is satisfied if a select number of color sample intensity thresholds are satisfied.

In other embodiments, the intensity threshold may be a comparison between the different color sample intensities. In one embodiment, the comparison may be between the highest calculated intensity and the lowest calculated intensity. If the difference between these calculated intensities is above a threshold amount (e.g., 0.3), then the intensity threshold is satisfied. In another embodiment, the comparison may be between each calculated intensity to determine if there is a sequential increase from one calculated intensity to the next from the lowest calculated intensity to the highest calculated intensity. The order of color sample intensities for this sequential increase is determined by the order of color samples on the color validation sheet.

In various embodiments, one or more of these or other thresholds may be utilized to determine if the red color set intensity satisfies the intensity threshold. For example, the intensity threshold may be satisfied if the color sample intensities sequentially increase and the difference between the lowest calculated intensity and the highest calculated intensity exceeds a select value.

If the red color set intensities satisfy the one or more intensity thresholds, then process 400 flows to block 414; otherwise, process 400 flows to block 424.

At block 414, an intensity of each of a plurality of color samples of a green color set on the color validation sheet is determined. In at least one embodiment, the color validation sheet includes seven different green sample intensities. The intensity of each of these sample colors is calculated.

Process 400 proceeds next to decision block 416, where a determination is made whether the intensities for the green color set satisfy one or more intensity thresholds. In various embodiments, decision block 416 may employ embodiments similar to decision block 414, but for the green color set. In some embodiments, the thresholds employed for the red color set may be the same for the green color set. In other embodiments, the thresholds may be modified or customized for the green color set. If the green color set intensities satisfy the one or more intensity thresholds, then process 400 flows to block 418; otherwise, process 400 flows to block 424.

At block 418, an intensity of each of a plurality of color samples of a blue color set on the color validation sheet is determined. In at least one embodiment, the color validation sheet includes seven different blue sample intensities. The intensity of each of these sample colors is calculated.

Process 400 proceeds next to decision block 420 where a determination is made whether the intensities for the blue color set satisfy one or more intensity thresholds. In various embodiments, decision block 420 may employ embodiments similar to decision block 414, but for the blue color set. In some embodiments, the thresholds employed for the red and green color sets may be the same for the blue color set. In other embodiments, the thresholds may be modified or customized for the blue color set. If the blue color set intensities satisfy the one or more intensity thresholds, then process 400 flows to block 422; otherwise, process 400 flows to block 424.

At block 422, an indication that the color is valid is returned. In at least one embodiment, the satisfied color validation may automatically begin or continue process 300 in FIG. 3. In other embodiments, the user is notified that the color validation process was successful. After block 422, process 400 may terminate or otherwise return to a calling process to perform other actions.

If, at decision blocks 412, 416, or 420, an intensity threshold is not satisfied, then process 400 flows from these decision blocks to block 424. At block 424, an indication that the color is invalid or a color validation error is returned. In some embodiments, the user is notified that the color validation process was unsuccessful. After block 424, process 400 may terminate or otherwise return to a calling process to perform other actions.

Although process 400 is describes a processing red, green, and blue color sets, embodiments are not so limited. In some embodiments, only a single color may be analyzed, two colors may be analyzed or a plurality of colors may be analyzed to determine if one or more intensity thresholds are satisfied. Moreover, other colors or numbers of color samples may also be utilized. In some embodiments, the image of the color validation sheet is converted into a grayscale image prior to calculating the color intensities.

FIGS. 5A-5D illustrate use case examples of graphical user interfaces presenting information to a user with respect to validating rapid test device results in accordance with embodiments described herein. In various embodiments, graphical user interfaces 500A-500D of FIGS. 5A-5D, respectively, may be presented on a rapid-test-validation computing device 124 of FIG. 1.

FIG. 5A illustrates a use case example of a graphical user interface 500A displaying an image having a rapid-test-device reference 502 overlaid on the received image. In this example, there is no physical rapid test device present in the presented image, such as before an image of a rapid test device is captured. As can be seen, the rapid-test-device reference 502 is a semi-transparent representation of a rapid test device superimposed on the image that is displayed to the user.

FIG. 5B illustrates a use case example of a graphical user interface 500B displaying an image having a physical or actual rapid test device 504 and a rapid-test-device reference 502 overlaid on the received image. In this example, the rapid test device 504 does not align with the rapid-test-device reference 502. Overlaying the rapid-test-device reference 502 on the image provides a guide that enables a user to move the rapid-test-validation computing device 124 into an acceptable position within the image wherein the actual rapid test device 504 is substantially aligned with the rapid-test-device reference 502 for the corresponding artificial intelligence mechanisms to be employed, as described herein.

FIG. 5C illustrates a use case example of a graphical user interface 500C displaying an output indicating that the test results 510 of the rapid test device 504 are invalid. Although not illustrated, in some embodiments, the graphical user interface 500C may display one or more notifications indicating possible reasons why the results are not valid.

FIG. 5D illustrates a use case example of a graphical user interface 500D displaying an output indicating an objective characterization of the test results 512 of the rapid test device 504. In this example, the graphical user interface 500D indicates that the test results 512 are "positive." Although not illustrated, in some embodiments, the graphical user interface 500D may display one or more notifications indicating what the particular results mean. For example, if the rapid test device outputs a plurality of results, the graphical user interface may display an objective characterization of each individual output and a cumulative result from the combination of all results.

Figure 6B:
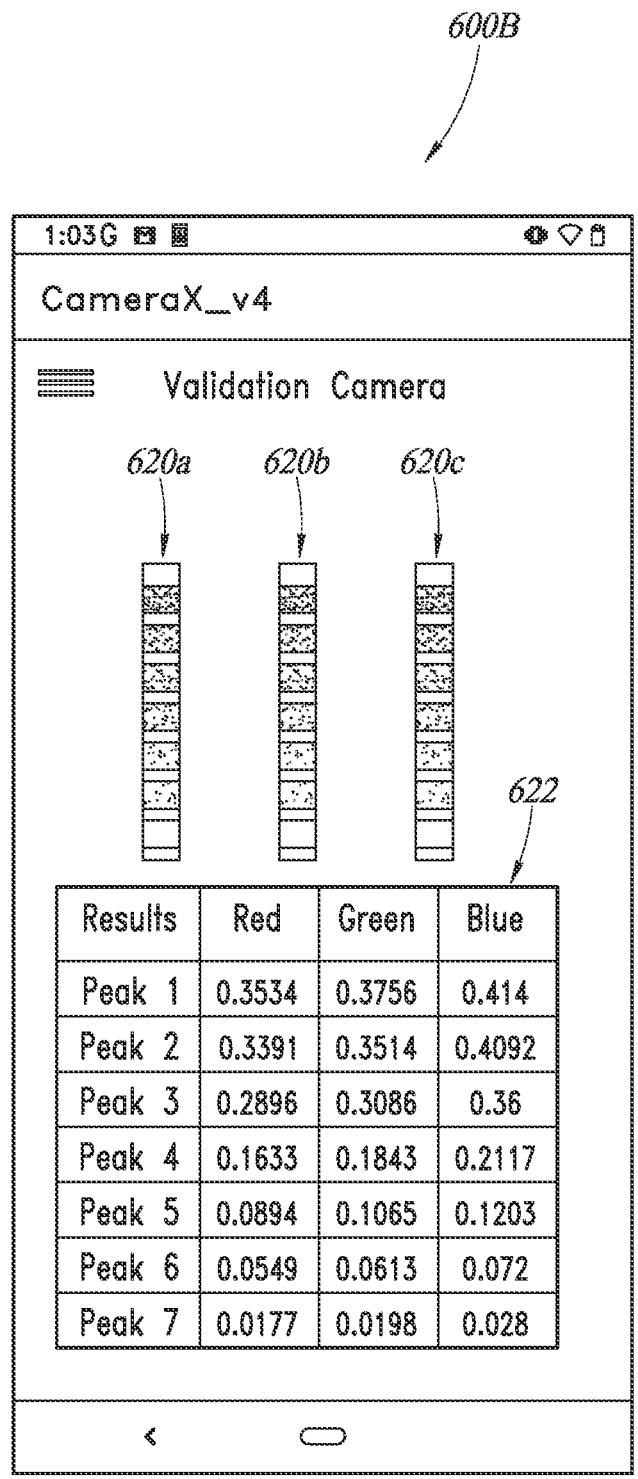

FIGS. 6A-6B illustrate use case examples of graphical user interfaces presenting information to a user with respect to validating camera colors prior to validating rapid test device results in accordance with embodiments described herein.

FIG. 6A illustrates a use case example of a graphical user interface 600A displaying an image having a physical or actual color validation sheet 602 and an alignment frame 604 overlaid on the received image. In this example, the color validation sheet 602 does not align with the alignment frame 604. Overlaying the alignment frame 604 on the image provides a guide that enables a user to move the rapid-test-validation computing device 124 or the color validation sheet 602 into an acceptable position within the image wherein the actual color validation sheet is substantially aligned with the alignment frame 604 for the corresponding artificial intelligence mechanisms to be employed, as described herein.

In this example, the color validation sheet 602 includes three color sample sets 606a-606c. Color sample set 606a is a red set that includes a plurality of different intensity samples 608a-608g. Sample 608a has the lowest red intensity and sample 608g has the highest red intensity for the set. The intensity of the samples 608a-608g sequentially increase from sample 608a to sample 608g. Color sample set 606b is a green set and color sample set 606c is a blue set, which both include a plurality of different intensity samples that sequentially increase from a lowest intensity to a highest intensity for each respective set (these samples are not individually referenced for clarity of the figure).

As described herein, the intensity of each color sample is determined, which is shown in FIG. 6B.

FIG. 6B illustrates a use case example of a graphical user interface 600B displaying results of the processing of the color samples from the color validation sheet 602 in FIG. 6A. Output 620a-620c illustrate grayscale intensities of the color samples determined from the color validation sheet 602. For example, output 620a is the grayscale intensities for the red color set 606a, output 620b is the grayscale intensities for the green color set 606b, and output 620c is the grayscale intensities for the blue color set 606c. The numerical values of these intensities is shown in table 622, which can be used to determine if the calculated intensities satisfy one or more intensity thresholds, as described herein. In some embodiments, the system may not display the numerical values of the determined intensities. Rather, in some embodiments, the system may display a "pass/fail" result without provide additional details as to the determined intensities.

The use of the color validation sheet enables the system to confirm that the camera is capturing images with colors having sufficient dynamic range to properly analyze rapid test devices, as described herein.

Figure 7:
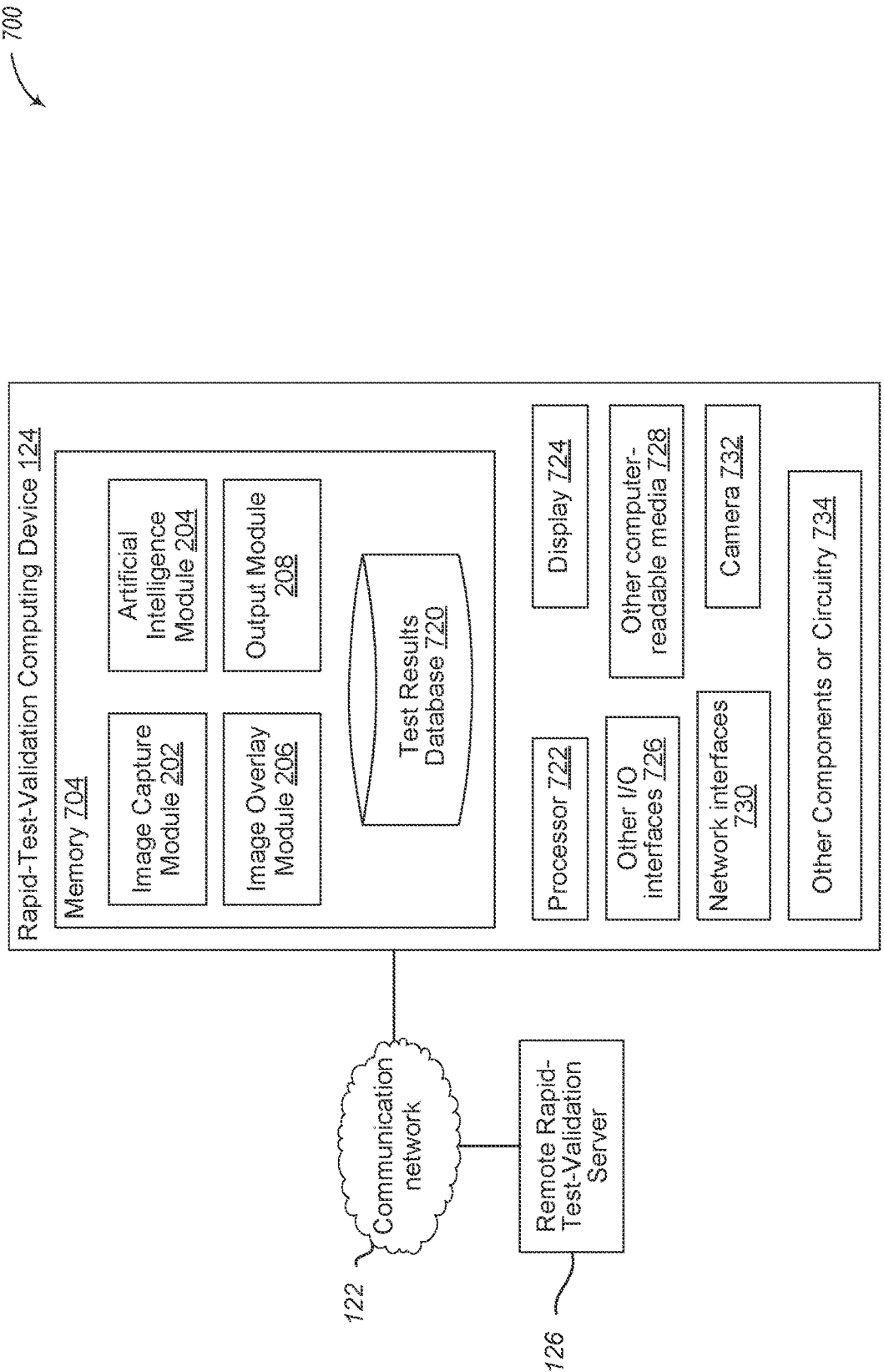
FIG. 7 shows a system diagram that describes various implementations of computing systems for implementing embodiments described herein.

FIG. 7 shows a system diagram that describe various implementations of computing systems for implementing embodiments described herein. System 700 includes rapid-test-validation computing device 124, and optionally remote rapid-test-validation server 126, similar to what is described in FIG. 1.

As described herein, the rapid-test-validation computing device 124 is a computing device that captures images of rapid test devices, employs a first artificial intelligence mechanism to determine a position of the rapid test device in the images, employs a second artificial intelligence mechanism to determine if the test results of the rapid test device are valid, and employs a third artificial intelligence mechanism to identify the test results of the rapid test device. In some embodiments, the rapid-test-validation computing device 124 captures images of a color validation sheet to determine if the colors captured by a camera of the rapid-test-validation computing device 124 are sufficient for processing images of rapid test devices. One or more special-purpose computing systems may be used to implement rapid-test-validation computing device 124. Accordingly, various embodiments described herein may be implemented in software, hardware, firmware, or in some combination thereof. The rapid-test-validation computing device 124 includes memory 704, one or more processors 722, display 724, input/output (I/O) interfaces 726, other computer-readable media 728, network interface 730, camera 732, other components or circuitry 734.

Processor 722 includes one or more processing devices that execute computer instructions to perform actions, including at least some embodiments described herein. In various embodiments, the processor 722 may include one or more central processing units ("CPU"), programmable logic, or other processing circuitry.

Memory 704 may include one or more various types of non-volatile and/or volatile storage technologies. Examples of memory 704 may include, but are not limited to, flash memory, hard disk drives, optical drives, solid-state drives, various types of random access memory (RAM), various types of read-only memory (ROM), other computer-readable storage media (also referred to as processor-readable storage media), or the like, or any combination thereof. Memory 704 may be utilized to store information, including computer-readable instructions that are utilized by processor 722 to perform actions, including at least some embodiments described herein.

Memory 704 may have stored thereon various modules, such as image capture module 202, artificial intelligence module 204, image overlay module 206, and output module 208. The image capture module 202 captures images of one or more rapid test devices using camera 732. The camera 732 includes one or more cameras that are configured to capture images of one or more rapid test devices.

The image overlay module 206 modifies the captured images to overlay a rapid-test-device reference on the images, which may include employing an artificial intelligence mechanism to identify rapid test devices included in the captured images. The artificial intelligence module 204 employs a plurality of artificial intelligence mechanisms to determine a position of the rapid test device in the image, determine if a test result of the rapid test device is valid, and to determine an objective characterization of the test results. The output module 208 presents the modified images, validation results, and the objective characterization of the test results to a user of the rapid-test-validation computing device 124.

The memory 704 may also store test results database 720, which includes configuration information for each employed artificial intelligence mechanism, test results, rapid test device information, etc.

The display device 724 may include one or more LCD screens, LEDs or other lights, or other types of display devices that present graphical user interfaces of information to a user (e.g., rapid-test-device reference overlaid images, validation results, test results, etc.). The other I/O interfaces 726 may include interfaces for various other input or output devices, such as audio interfaces, video interfaces, USB interfaces, physical buttons, keyboards, or the like.

The other computer-readable media 728 may include other types of stationary or removable computer-readable media, such as removable flash drives, external hard drives, or the like.

The network interfaces 730 are configured to communicate with other computing devices, such as the remote rapid-test-validation server 126. Network interfaces 730 include transmitters and receivers (not illustrated) to send and receive data as described herein.

The other components or circuitry 734 may include other computing components, application-specific integrated circuits (ASICs), digital signal processors, discrete circuitry, logic gates, standard integrated circuits, controllers (e.g., by executing appropriate computing instructions, and including microcontrollers or embedded controllers), field-programmable gate arrays (FPGAs), complex programmable logic devices (CPLDs), etc., that can employ at least some embodiments described herein.

The remote rapid-test-validation server 126 includes a special-purpose computing system that may be used to communicate with the rapid-test-validation computing device 124 to provide at least some embodiments described herein. The remote rapid-test-validation server 126 may receive images from and provide results to the rapid-test-validation computing device 124 via communication network 122 in accordance with embodiments described herein. Accordingly, in some embodiments, the remote rapid-test-validation server 126 includes computing components similar to those of the rapid-test-validation computing device 124 such that various embodiments described herein may be implemented in software, hardware, firmware, or in some combination thereof.

The various embodiments described above can be combined to provide further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method, comprising:
obtaining one or more first images of a rapid test device;
overlaying a semi-transparent reference of the rapid test device on the one or more first images;
presenting the one or more overlaid images to a user in real time as the one or more first images are being obtained;
employing a first artificial intelligence mechanism to determine a position of the rapid test device in the one or more first images relative to the semi-transparent reference in response to identification of the rapid test device, wherein the first artificial intelligence mechanism is trained to identify the rapid test device;
responsive to the position of the rapid test device being in an acceptable position relative to the semi-transparent reference in at least one of the one or more first images:
capturing a second image of the rapid test device;
employing a second artificial intelligence mechanism on the second image to determine if a result of the rapid test device is valid, wherein the second artificial intelligence mechanism is trained to classify valid or invalid test results output by the rapid test device;
responsive to the result of the rapid test device being invalid, presenting an invalid-test-result notification to the user;
responsive to the result of the rapid test device being valid, employing a third artificial intelligence mechanism on the second image to determine an objective characteristic of the result of the rapid test device, wherein the third artificial intelligence mechanism is trained to classify possible objective characteristics output by the rapid test device; and
presenting the objective characteristic of the result to the user.

2. The method of claim 1, wherein capturing the second image of the rapid test device comprises:
selecting the second image from the one or more first images that includes the rapid test device being in the acceptable position.

3. The method of claim 1, further comprising:
storing the second image in a database along with an indication of whether the result of the rapid test device is valid or invalid and an indication of the objective characteristic of the result of the rapid test device.

4. The method of claim 1, wherein presenting the objective characteristic of the result includes:
presenting an indication of a positive or negative result.

5. The method of claim 1, wherein overlaying the semi-transparent reference of the rapid test device on the one or more first images comprises:
receiving an indication of a type of the rapid test device from the user; and
selecting the semi-transparent reference from a plurality of semi-transparent references based on the received selection.

6. The method of claim 1, wherein employing the third artificial intelligence mechanism on the second image comprises:
determining a type of the rapid test device from a plurality of types rapid test devices; and
selecting the third artificial intelligence mechanism from a plurality of artificial intelligence mechanisms based on the determined type of the rapid test device.

7. The method of claim 1, further comprising:
prior to obtaining the one or more first images of the rapid test device:
capturing a fourth image of an identifier of the rapid test device;
initiating a timer associated with the rapid test device based on the identifier; and
wherein obtaining the one or more first images of the rapid test device is responsive to expiration of the timer.

8. The method of claim 1, further comprising:
prior to obtaining the one or more first images of the rapid test device:
capturing a fourth image of a color validation sheet;
determining a color intensity for each of a plurality of color samples for multiple color sets;
determining if the determined color intensities satisfy one or more thresholds;
responsive to the determined color intensities not satisfying the one or more thresholds, presenting an indication of a non-satisfied color threshold; and
wherein obtaining the one or more first images of the rapid test device is responsive to the determined color intensities satisfying the one or more thresholds.

9. A rapid-test-validation computing device, comprising:
a memory that stores computer instructions; and
a processor that executes the computer instructions to:
present a semi-transparent reference of a rapid test device to a user;
obtain one or more first images of the rapid test device;
employ a first artificial intelligence mechanism to determine a position of the rapid test device in the one or more first images relative to the semi-transparent reference;
responsive to the position of the rapid test device being in an acceptable position relative to the semi-transparent reference in at least one of the one or more first images:
capture a second image of the rapid test device;
employ a second artificial intelligence mechanism on the second image to determine if a result of the rapid test device is valid;
responsive to the result of the rapid test device being invalid, present an invalid-test-result notification to the user;
responsive to the result of the rapid test device being valid, employ a third artificial intelligence mechanism on the second image to determine an objective characteristic of the result of the rapid test device; and
presenting the objective characteristic of the result to the user.

10. The rapid-test-validation computing device of claim 9, wherein the processor captures the second image of the rapid test device by further executing the computer instructions to:

select the second image from the one or more first images that includes the rapid test device being in the acceptable position.

11. The rapid-test-validation computing device of claim 9, wherein the processor further executes the computer instructions to:
store the second image in a database along with an indication of whether the result of the rapid test device is valid or invalid and an indication of the objective characteristic of the result of the rapid test device.

12. The rapid-test-validation computing device of claim 9, wherein the processor presents the semi-transparent reference of the rapid test device by further executing the computer instructions to:
receive an indication of a type of the rapid test device from the user; and
select the semi-transparent reference from a plurality of semi-transparent references based on the received selection.

13. The rapid-test-validation computing device of claim 9, wherein the processor employs the third artificial intelligence mechanism on the second image by further executing the computer instructions to:
determine a type of the rapid test device from a plurality of types rapid test devices; and
select the third artificial intelligence mechanism from a plurality of artificial intelligence mechanisms based on the determined type of the rapid test device.

14. The rapid-test-validation computing device of claim 9, wherein the processor further executes the computer instructions to:
prior to obtaining the one or more first images of the rapid test device:
capture a fourth image of an identifier of the rapid test device;
initiate a timer associated with the rapid test device based on the identifier; and
obtain the one or more first images of the rapid test device are obtained responsive to expiration of the timer.

15. The rapid-test-validation computing device of claim 9, wherein the processor further executes the computer instructions to:
prior to obtaining the one or more first images of the rapid test device:
capture a fourth image of a color validation sheet;
determine a color intensity for each of a plurality of color samples for multiple color sets;
determine if the determined color intensities satisfy one or more thresholds;
responsive to the determined color intensities not satisfying the one or more thresholds, present an indication of a non-satisfied color threshold; and
wherein the one or more first images of the rapid test device are obtained responsive to the determined color intensities satisfying the one or more thresholds.

16. A nontransitory processor-readable storage medium storing instructions that, when executed, cause a rapid-test-validation computing device to perform actions, the actions comprising:
prior to obtaining an image of a rapid test device:
capturing a second image of an identifier of the rapid test device; and
initiating a tinier associated with the rapid test device based on the identifier; and
in response to expiration of the tinier:
obtaining the image of the rapid test device;
employing a first artificial intelligence mechanism on the image to determine if a result of the rapid test device is valid;
responsive to the result of the rapid test device being invalid, presenting an invalid-test-result notification to a user;
responsive to the result of the rapid test device being valid, employing a second artificial intelligence mechanism on the image to determine an objective characteristic of the result of the rapid test device; and
presenting the objective characteristic of the result to the user.

17. The nontransitory processor-readable storage medium of claim 16, wherein the instructions, when executed, cause a rapid-test-validation computing device to perform further actions, the further actions comprising:
storing the image in a database along with an indication of whether the result of the rapid test device is valid or invalid and an indication of the objective characteristic of the result of the rapid test device.

18. The nontransitory processor-readable storage medium of claim 16, wherein the instructions, when executed, cause a rapid-test-validation computing device to perform further actions, the further actions comprising:
receiving a selection of the rapid test device from the user; and
selecting the first and second artificial intelligence mechanisms based on the received selection.

19. The nontransitory processor-readable storage medium of claim 16, wherein employing the second artificial intelligence mechanism on the image comprises:
determining a type of the rapid test device from a plurality of types rapid test devices;
selecting the first artificial intelligence mechanism from a first plurality of artificial intelligence mechanisms based on the determined type of the rapid test device; and
selecting the second artificial intelligence mechanism from a second plurality of artificial intelligence mechanisms based on the determined type of the rapid test device.

* * * * *